United States Patent [19]

Komatsu et al.

[11] Patent Number: 5,586,262
[45] Date of Patent: Dec. 17, 1996

[54] IMAGE DATA MANAGEMENT SYSTEM PARTICULARLY FOR USE IN A HOSPITAL

[75] Inventors: Kenichi Komatsu, Nishinasuno-machi; Eitaro Nishihara, Otawara; Kiyoshi Tawara, Otawara; Seiji Fujimoto, Otawara, all of Japan

[73] Assignee: Kabushiki Kaisha Toshiba, Kawasaki, Japan

[21] Appl. No.: 376,664

[22] Filed: Jan. 23, 1995

Related U.S. Application Data

[63] Continuation of Ser. No. 988,359, Dec. 7, 1992, abandoned, which is a continuation of Ser. No. 841,301, Feb. 28, 1992, abandoned, which is a continuation of Ser. No. 489,879, Mar. 7, 1990, abandoned, which is a continuation of Ser. No. 69,218, Jul. 2, 1987, abandoned.

[30] Foreign Application Priority Data

Jul. 2, 1986 [JP] Japan ................................ 61-154086
Jul. 2, 1986 [JP] Japan ................................ 61-154087

[51] Int. Cl.[6] .................................................. G06F 15/2
[52] U.S. Cl. ............................................ 395/200.02
[58] Field of Search ........................ 364/413.01, 413.02, 364/413.13; 382/6; 395/600, 200.02, 200.13, 600

[56] References Cited

U.S. PATENT DOCUMENTS 4,186,438  1/1980  Benson et al. ......................... 364/200
4,558,211 12/1985  Berstein ................................ 235/380

FOREIGN PATENT DOCUMENTS 0099978  2/1984  United Kingdom.

OTHER PUBLICATIONS

Enclopedia of Computer Science and Engineering Van Nostrand Reinhold Inc., 1983, pp. 563–565.

Dwyer et al. (pp. 194–204) SPIE vol. 318 (1982) (Part I) Picture Archiving & Communication Systems (PACS) for Medical Applications.

Walsh, M. E. *Database and Data Communication Systems* Reston, VA, Reston Pub. Co., 1983. pp. 205–212.

Everest, *Database Management*, p. 746 Date of Pub. Unknown, Publisher Unkown.

*Primary Examiner*—Gail O. Hayes
*Attorney, Agent, or Firm*—Oblon, Spivak, McClelland, Maier & Neustadt, P.C.

[57] ABSTRACT

An imaging system in a hospital includes plural diagnostic units each having a picture filing memory in which medical picture data of patients are stored. The memories are located in the diagnostic units at dispersed locations in the hospital. Each diagnostic unit includes a retrieval unit by which image data can be retrieved from the respective memory. A network interconnects the diagnostic unit and permits transmission of image data among the diagnostic units.

2 Claims, 6 Drawing Sheets

IMAGE DATA MANAGEMENT SYSTEM PARTICULARLY FOR USE IN A HOSPITAL

This application is a continuation of application Ser. No. 07/988,359, filed on Dec. 7, 1992, now abandoned which is a Con of Ser. No. 07/841,301 filed Feb. 28, 1992 now abandoned which is a Con of Ser. No. 07/489,879 filed Mar. 7, 1990 which is a Con of Ser. No. 07/069,218 filed Jul. 2, 1987 now abandoned.

BACKGROUND OF THE INVENTION

1. Field of the Invention

The present invention relates to an image data management system to be installed in a hospital.

2. Discussion of Background

In modern hospitals increasingly sophisticated digital imaging systems are being produced for and purchased by diagnostic radiology departments. Department space limitations frequently result in the geographic separation of these imaging systems to various floors or even buildings within a medical center. Additionally, the referring clinical staff have become more knowledgeable and more demanding in their diagnostic requests. These various factors have increased the need for an image information data management system that can:

(a) produce analog and/or digital images from various diagnostic technologies, (b) collate and/or integrate image information from multiple diagnostic technologies, (c) store digital diagnostic images, and (d) retrieve digital diagnostic images.

So there arises a need to store, collect, retrieve, display, process and treat images formed at the various modalities of the hospital, such as X-ray film images, X-CT (computed tomography) images, MRI (magnetic resonance imaging) images, RI(radioisotope) pictures, CR (computed radiography) images, US (ultrasound) images, endoscope pictures, and thermography images. Efforts to fulfill this need originated with the Picture Archiving & Communication System (hereinafter called PACS) for university hospitals, an experimental digital picture transmission system developed at Kansas University. Here, retrieval at 10 Mbits/sec was carried out in the Local Area Network of (hereinafter called LAN) of approximately 800 Mbytes of digital picture data formed each day. A technique to increase the picture transmission efficiency was produced to a state to be handed over to other universities. The field has advanced to a point where a perspective on image transmission, propriety of CRT diagnosis and large-capacity data archiving and retrieval have begun to be realized.

SUMMARY OF THE INVENTION

Accordingly, an object of the present invention is to provide a new and improved image data management system in which image data is efficiently stored and efficiently routed for display to various locations in a hospital.

The above object is accomplished by providing a novel image data management system for managing image data, including plural image data generating sections each having at least one modality for generating diagnostic image data; plural filing systems associated with and located at each of the sections; a network for interconnecting the modality of each section to the filing system of the respective section; and at least one viewing station connected to the network for viewing a diagnostic image based on image data retrieved from a selected filing system via the network.

Generally speaking, the present invention provides a new and improved database management system for a hospital, wherein image data obtained by functionally diverse units within the hospital are stored and maintained in filing systems dedicated to the units in which the image data are respectively obtained, and transferred between units as the need arises. Each unit obtains and maintains records on patients, whether on an impatient or an outpatient basis. When a patient returns to the hospital, his prior records can be retrieved from the filing system of each functionally diverse unit via the system network.

According to the invention, the network includes a high speed portion for transfer of data from an image data generating section to a viewing station associated with that section within the same facility and a low speed portion for transfer of data between sections of different facilities.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
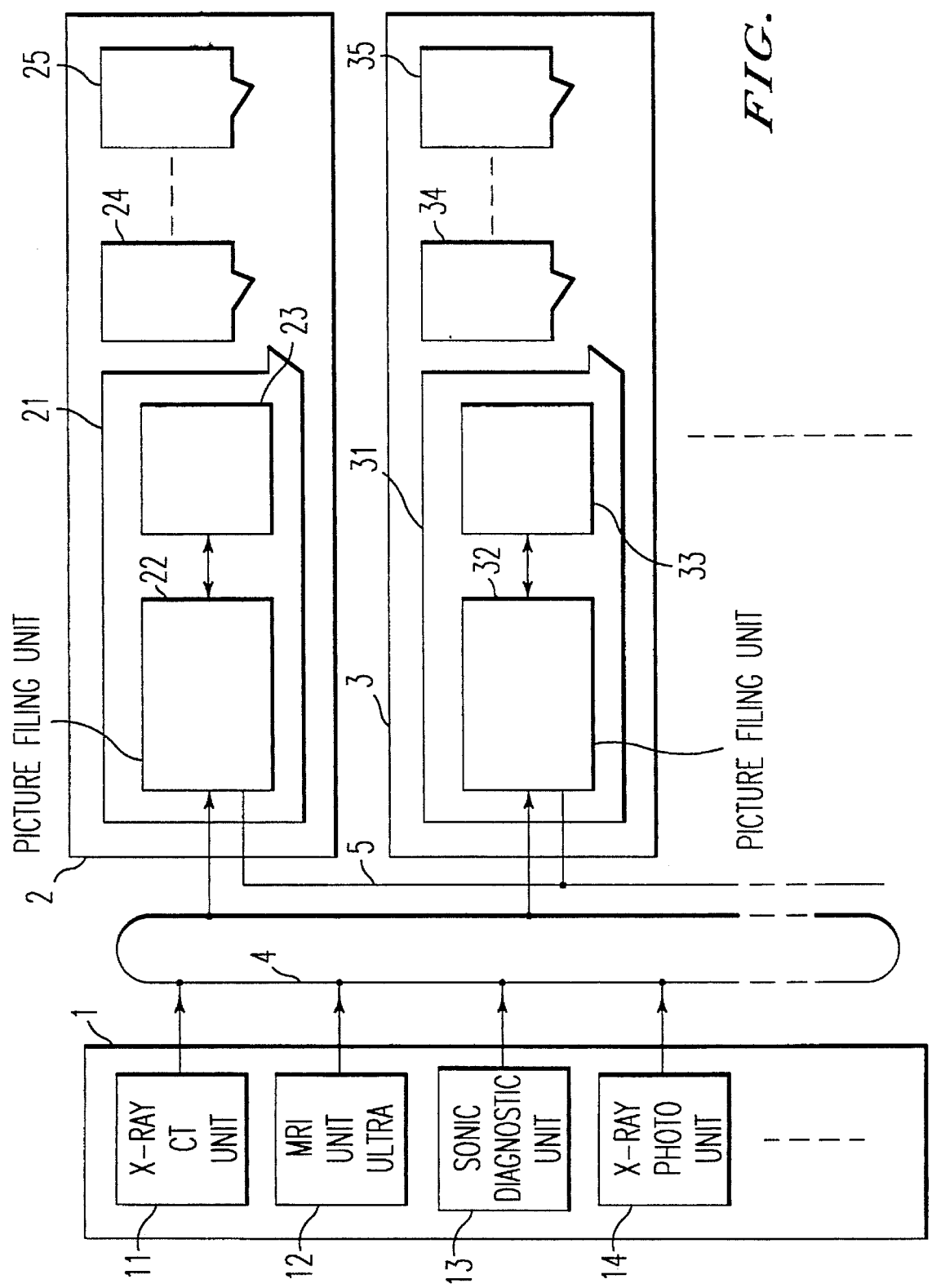
FIG. 1 is a block diagram showing a first embodiment of an imaging system in a hospital according to the present invention.

Referring now to the drawings, wherein like reference numerals designate identical or corresponding parts throughout the several views, and more particularly to FIG. 1, thereof, the first embodiment in the present invention is explained.

The central radiographic section 1 in FIG. 1 is provided with various modalities, such as an X-ray CT unit 11, a MRI unit 12, an ultrasonic diagnostic unit 13, and an X-ray photographing unit 14. In this central radiographic section 1, signals to be obtained from outpatients and inpatients are sent out to the network 4 by converting the signals to respective image data in each modality.

Figure 2:
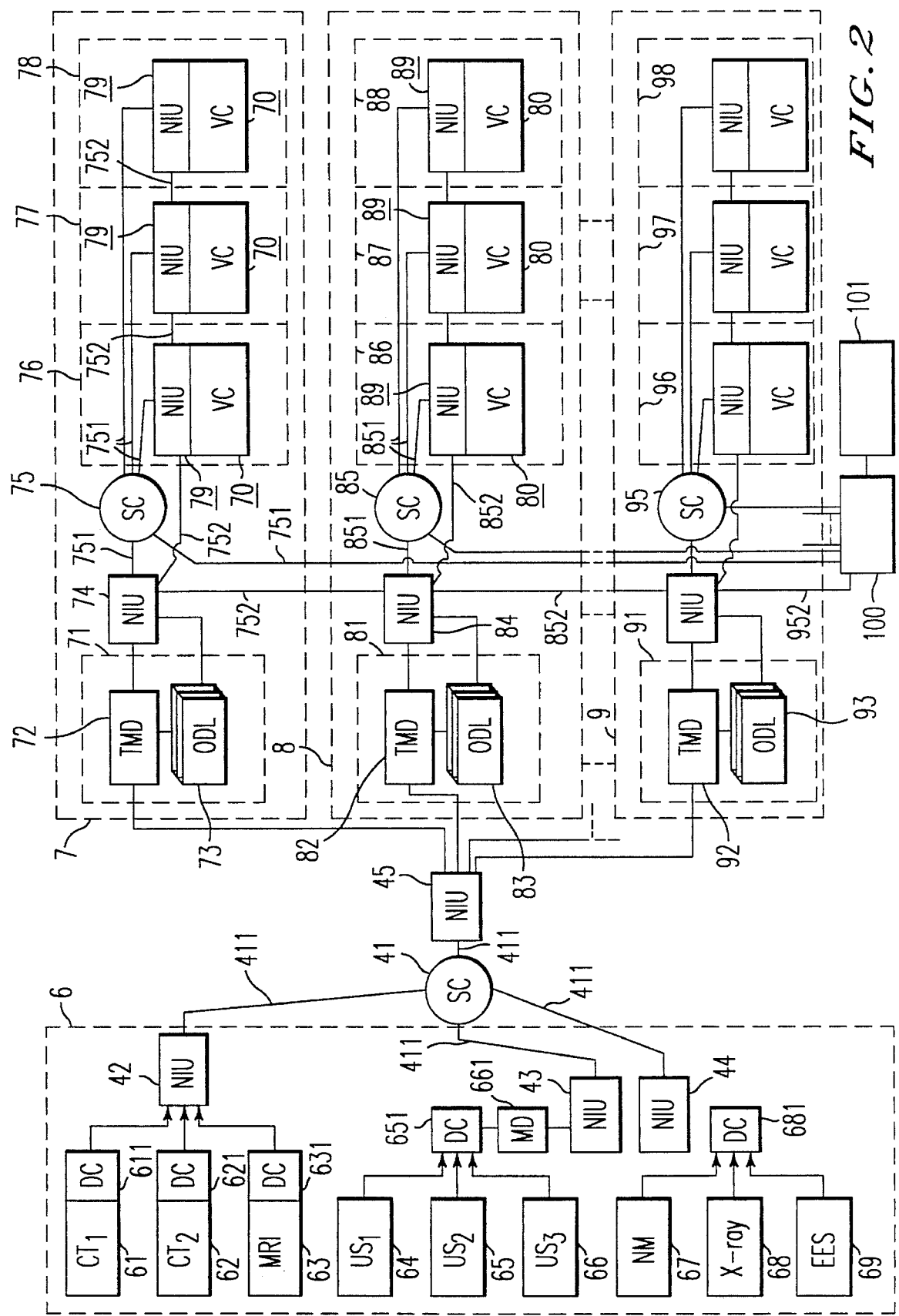
FIG. 2 is a block diagram showing a second embodiment of an imaging system according to the present invention.

As shown in FIG. 1, picture filing units 22 and 32 are additionally connected to the network 4. Then, pictures formed by each modality are sent to picture filing units 22 and 32 through this network 4. At this time, image data of each patient are controlled so as to be transferred to a picture filing unit installed in the section to which the attending physician belongs. This control is carried out by a network interface unit (NIU) 45, as shown in FIG. 2.

In the filing room 21 of the first medical ward a picture filing unit 22 and a retrieval unit 23 are installed. Sent to the picture filing unit 22 are picture data of outpatients for which a first physician is in charge, and for example, picture data of patients hospitalized in wards 24 and 25 are sent to the unit 22.

The picture filing unit 22 and retrieval unit 23 are closely connected, and patient picture data in the same facility can be read at high speed. In another filing room 31 at a second medical ward is provided another picture filing unit 32, to which picture data of outpatients under the care of a second physician are sent.

In a hospital organized in such a way, by managing the picture data section by section, not only is the place of storage distributed according to the kind of image, but also the systematic management of images on the same patient may be easily performed.

Further, in case there are many data to be managed by a facility, for example, by means of optical discs managed by removing the optical discs from an automatic changer and placing them on a shelf, it is enough that a nurse or information controller in the facility transfers optical discs to the autochanger. Where optical discs have been transferred to the autochanger, an outpatient after several years may return to the hospital again. Then it is typically a troublesome task to retrieve his prior image data, However, the frequency of occurrence of this happening is generally low in view of the total ratio.

In the conventional integrated central filing system, an outpatient's return to the hospital is communicated from the patient reception area to the integrated central filing room.

In particular, hospitals, especially large hospitals, manage patients by section. For that reason, too, it is desirable to manage picture data by section. Further, where picture data is managed by modality, picture data of the same patient are spread over plural modalities, and the data management becomes more complicated.

Therefore, if the image data management system of constitution like the present invention is adopted, in addition to the above-mentioned advantages, it is excellent in system expandability and flexibility, and the system construction becomes easy.

For that reason, since the present system has application ranging from a small hospital with two subfacilities to a large hospital with more than 1,200 beds, but is also easily implemented as a system in a unit of a facility even in a relatively large hospital now in operation, the system construction can be expanded to cover larger and larger numbers of units and facilities in a hospital.

Picture filing units 22 and 32 are connected by the network 5, and both can receive data. However, the transfer of data to and from another facility is relatively infrequent compared with data transfers within the same facility. For that reason, the network between facilities is connected more roughly than the network for transfer in the facility.

The following methods are used to closely connect the file and retrieval unit in each file (hereinafter called intra-section or intra-facility communication) and roughly connect them between sections (hereinafter called inter-section or inter-facility communication):

(A) The data transfer on the intra-section network is sent at higher speed than the inter-section communication. For example, the intra facility communication is sent at data transfer rate of 20 Mbytes/second through optical fibers, and on the other one hand, in the inter-section communication the data of 0.5 Mbyte/second is transferred by the coaxial cable.

(B) The in-section communication and the inter-section communication are connected by the same network, the transfer rate is made same, the priority of the inter-section communication is lowered, and the data is transferred.

(C) When the data transfer is carried out from another section, the protocol for obtaining the permission of the opposite party or the keyword input is stored in advance in retrieval units 23 and 33. In this way, the time for retrieval of image data located at the other section becomes substantially longer.

(D) A repeater or gate way is added and connected to the network of inter-section communication, and the information between sections is carried out through the repeater or gate way.

If any of the above-mentioned (A) to (D) are employed, there is no hinderance in the frequent retrieval in the intra-section communication, and the data transfer between sections is carried out.

The retrieval time in the present invention corresponds to the time from the start of the retrieval retrieval until the retrieved image is displayed.

Next, the second embodiment of the present invention is shown in FIG. 2 and explained as follows.

The central radiography section 6 is provided with X-ray CT units 61 and 62, MRI unit 63, supersonic diagnostic units 64, 65 and 66, NM unit 67, X-ray photographing unit 68, and endoscope unit 69. These units are installed in plural rooms, detect signals from inpatients and outpatients, visually display the signals and output them as image data.

To modalities 61, 62 and 63 De (Data Compression) units 611, 621, and 631 are connected. The DC unit compresses the image data from the respective modality, and outputs it to the NIU (Network Interface Unit) 42.

On the one hand, since ultrasonic diagnostic units 64, 65 and 66 have the same data output format, a single DC (data compression) unit 651 is sufficient. Then, the output from the DC 651 is temporarily stored by the magnetic disc (MD) 661 and waits until the network to be connected to the output is released. In this way, collisions in the network can be avoided. Since other modalities 61, 62 and 63 are provided with internal memories, MDs are not in particular required.

The network system connected to the central radiography section 6 is provided with optical fibers 411 to connect NIUs 42, 43, 44 and star coupler (SC) 41, and between SC41 and NIU 45 in star form. Then, image data compressed from NIUs 42, 43 and 44 at the modality side are transferred to the NIU 45 installed at the picture filing side through the optical fiber 411 and SC 41. The NIU 45 converts optical signals to electric signals, and also carries out the control of the network.

The control is effectively carried out so that signals from NIUs 42, 43 and 44 do not collide.

Numerals 7, 8 and 9 shown in FIG. 2 designate facilities subdivided in a hospital (for example, by diagnostic item), composed of a first internal department, a second internal department, and a first surgery department. Since medical fields other than these, for example, obstetrics, pediatrics, ophthalmology, etc,. are basically the same constitution as the first internal department, these are abbreviated.

It is possible to group together closely related facilities in one section or even in sections with small number of beds, even if not related as one diagnostic unit.

Such plural sections can be in different buildings, respectively, divided by different floors, of commonly located in the unit of each section.

Facilities 7 and 8 are provided with picture filing units 71 and 81, medical offices 76 and 86, wards 77 and 87, and consultation rooms 78 and 88 for outpatients. Then, picture filing units 71 and 81, medical offices 76 and 86, wards 77 and 87, and consultation rooms 78 and 88 of each section are closely connected to NIUs 74, 79, 84 and 89 by the network system employing star couplers 75 and 85, respectively.

The picture data from each modality is transferred through the network to picture filing units 71, 81 and 91 of sections to which the patient belongs.

The picture filing unit 71 is provided with a Temporary Magnetic Disc (TMD) provided with a memory by which rewrite is possible (for example, magnetic disc and RAM) and an Optical Disc Library (ODL) with a memory in which rewrite is impossible (for example, optical disc). The ODL is provided with a shelf to store an autochanger (not illustrated) and optical discs that cannot be stored by the autochanger. Both the TMD 72 and the 73 are connected, and also connected to the NIU 74. Further, the TMD 72 is divided into image data for inpatients and image data for outpatients according to patients, respectively. Then, image data for inpatients are mainly sent to the viewing console (VC) 70 of ward 77 and image data for outpatients to the VC 70 installed in the consultation room 78.

The management of picture files is divided into that for inpatients and that for outpatients, and data flows smoothly, by transferring them to the specified places, respectively. The TMD 72 is also connected to the NIU 45 and the image data from the central radiography section 6 is stored in the memory through the NIU 45.

In each of the medical office 76, ward 77, and consultation room 78, a NIU 79 and viewing console (VC) 70 are installed. Physicians and/or patients can see image data obtained from the central radiography section 6, by reproduction and display via the VC 70.

The VC 70 is, for example, a monitor which produces a picture display. In particular, the diagnostic VC 70 installed in the medical office has a picture processor not illustrated, and displays the image data stored in the TMD 72 after the data undergoes picture processing (for example, luminance conversion, addition of Schemer or ROI, magnification, emphasis, and multi-imaging application). In this way, since a physician can see pictures of each patient in an optimum condition, he can make the diagnosis more precisely.

In each section, the data transfer is carried out simply employing SC 75 and 85, respectively, and controlled by NIUs 74 and 84 so as to be effectively transferred without data collision between plural NIUs. The data transfer technique in this case is in accordance with the Gazette U.S. Patent application Ser. No. 806,375, filed Dec. 9, 1985. In this Gazette application a technique to perform the data transfer between NICs by installing optical fibers 751 and 851 for exclusive use of picture data transfer and transmission lines 752, 852 and 952 for exclusive use of control data to effectively transfer picture data, is disclosed.

Network systems using the Gazette technique are installed in each section, and network systems of each section are connected by installing repeaters 100 between the sections. The repeater 100 transmits data from one of SCs 75, 85 and 95 to others of SCs 75, 85 and 95. The control of the repeater 100 is carried out by lowering the priority of the transmission lines 751 and 851 relative to the control transmission line 952 and the supervisor 101. Further, the repeater 100 is provided with a buffer memory not illustrated, and controlled by the supervisor 101 so as to instruct data transmission to the destination or temporary data storage in the buffer memory when the data transfer destination is in use and data transfer cannot be done until the use is released. In such a way, by connecting networks through a repeater, the communication between sections can be done without interfering with the data transfer of transmission line 751 and 851.

Figure 4:
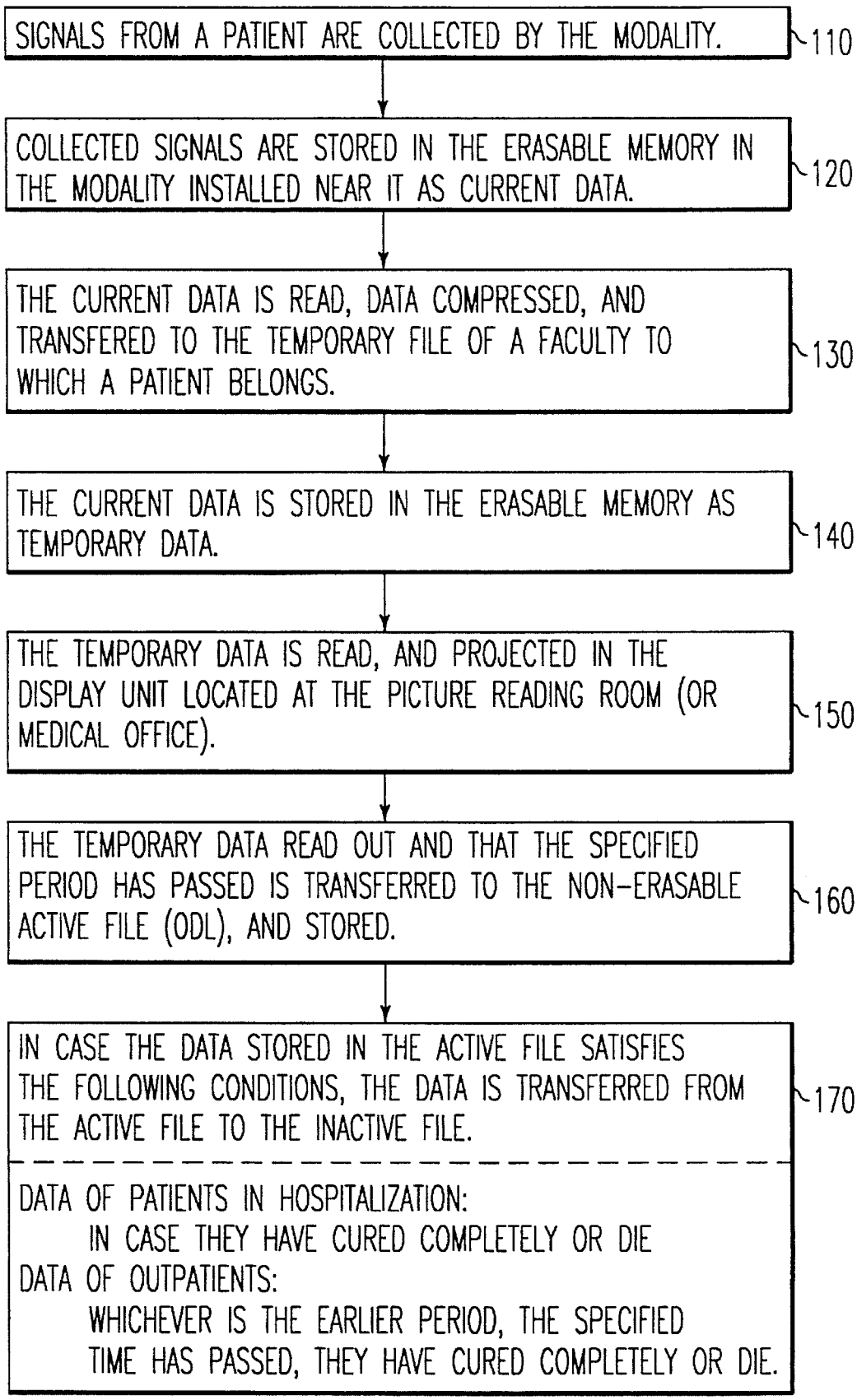
FIG. 4 shows a flow chart illustrating an example of operation of an imaging system according to the present invention in a hospital.

Now, in order that the present invention can be more readily understood, explanation is provided by the flow chart shown in FIG. 4.

Step 110

First, signals from patients are collected by the modality, and image data are elaborated. At this time, it is known whether the patients are inpatients or outpatients, or to which section they belong. Such information can be obtained from the patient ID and the input data from each modality.

Step 120

Signals collected in the modality are stored in the erasable memory in the modality near it as current data.

Step 130

Picture data from each modality are transferred to picture filing units 71, 81 and 91 of the section to which the patient belongs through the network system.

Step 140

In filing units 71, 81 and 91 section data are stored by distributing them further for inpatients and for outpatients. Image data from the NIU 45 are transferred to TMDs 72, 82 and 92 of the section(s) to which the patient belongs (1 section or plural sections), and entered into the erasable memory.

Step 150

It is supposed, for example, that the patient (tentatively called Mr. A) at this time is an outpatient who receives a diagnostic test only in the first internal department. Then, both data of tomographic images and photographic pictures of Mr. A are compressed by the X-ray CT unit 61 and X-ray photographing unit 68, and stored in the erasable memory of TMD 72 located at the first internal department 7. Further, the data is temporarily stored in the data area for outpatients.

An instruction by the input from the VC 70 located at the image reading room not illustrated or the medical office 76 is read from the erasable memory of TMD 72, and immediately sent through NIUs 74 and 79.

The image data sent from the TMD 72 to the VC 70 of medical office 76 is restored to the origin and displayed on the VC 70 as a visible picture. In particular, since this VC 70 is provided with a picture processor, a physician can edit pictures arbitrarily while seeing the edited pictures.

Step 160

Pictures of Mr. A still remain stored in the TMD 72. When a patient is diagnosed in outpatient room is given from the VC 70 located at the room for outpatients 78 to the TMD 72, and image data, are transferred to the ODL 73. After transfer, picture data transferred to the TMD 72 are erased to secure an area where next image data are stored.

Then, suppose that Mr. A shall be hospitalized, and transferred from the outpatient room to a ward. Then, image data of Mr. A previously obtained from that point of time are entirely transferred from the ODL 73 to the disk (not illustrated) attached to the VC for diagnostic use by the ward. At this time, image data of Mr. A are stored in the file for hospitalization by time sequence in the order obtained by the modality. Since the disk (not illustrated) in which the data is stored has a smaller storage capacity and smaller access time compared with the ODL 73, the retrieval time from the VC 70 becomes short. Therefore, image data of comparatively high frequency of use of the data remain stored in the disk (not illustrated).

Suppose that Mr. A is cured in the ward 77 of first internal department 7 and leaves the hospital. Thereupon, his data are transferred to the optical disc shelf from the optical disc autochanger located at the inside of the ODL 73. This transfer may be done by the mechanical transportation means, automatically, or manually by a responsible person in management of the filing unit 71 in the first internal department.

Step 170

Such a data transfer to the shelf is performed not only at the time of leaving the hospital, but also in case a patient dies, an outpatient has been cured completely, or when a specified period (for example, 6 months) has passed.

With the above description, an embodiment of the present invention has been described, but the present invention is not limited to this embodiment, but can be employed by changing it in various ways.

Figure 3:
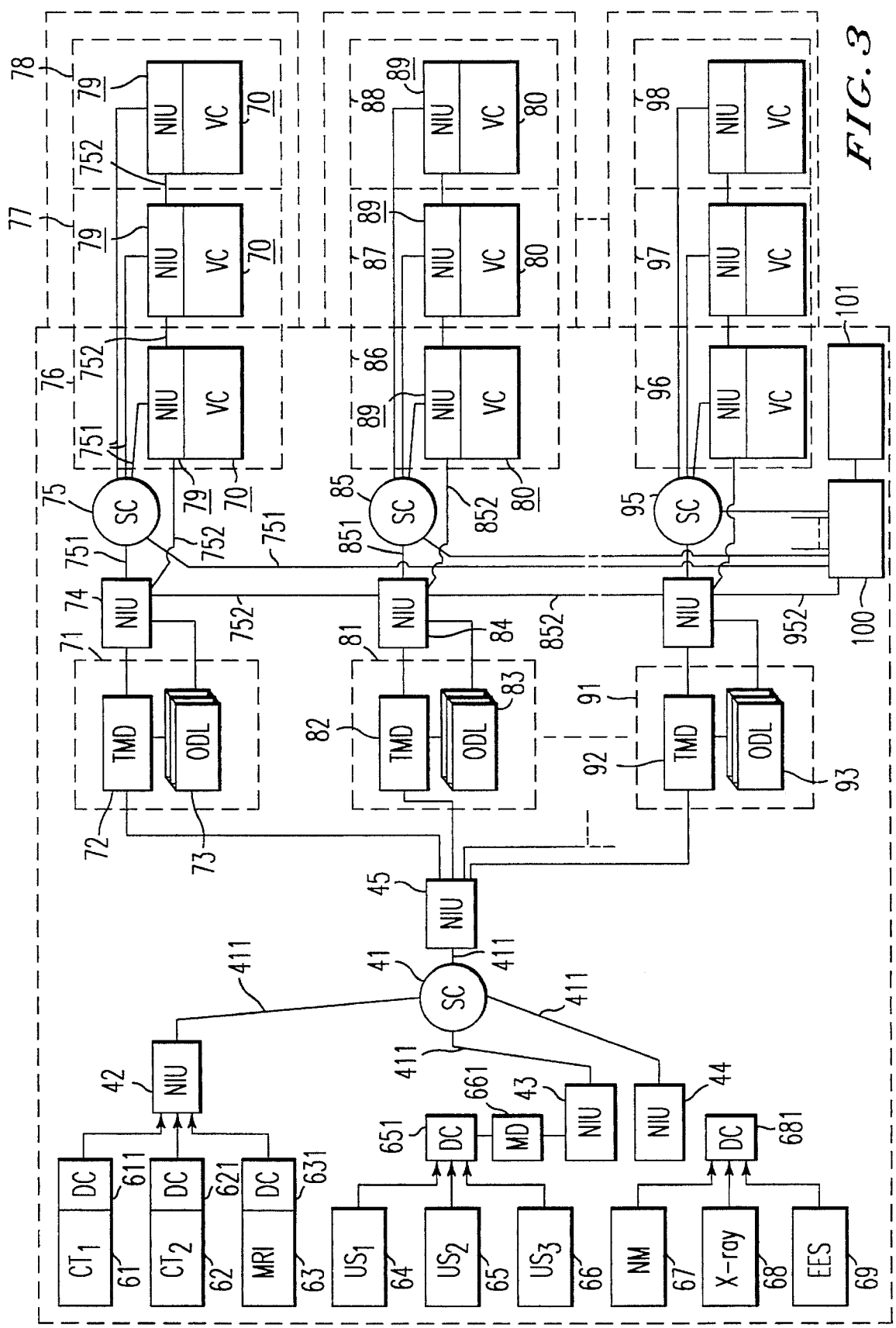
FIG. 3 is a block diagram showing a third embodiment of an imaging system according to the present invention.

For example, the radiography section includes also picture filing units 71, 81 and 91 and medical offices 76, 86 and 96 of each facility as shown in FIG. 3. Further, it is also noted that:

(1) The network used for mutual connection of facilities and modalities is not limited to the star coupler system by the above description, but other network interconnection means may be employed.

(2) When the amount of data communication is small, it is possible to integrate everything into one and the same network.

(3) It is possible to organize image data filing by part of, and not necessarily all of, a facility.

In such a way, the present invention can be changed diversely according to the construction and organization of each hospital.

Figure 5:
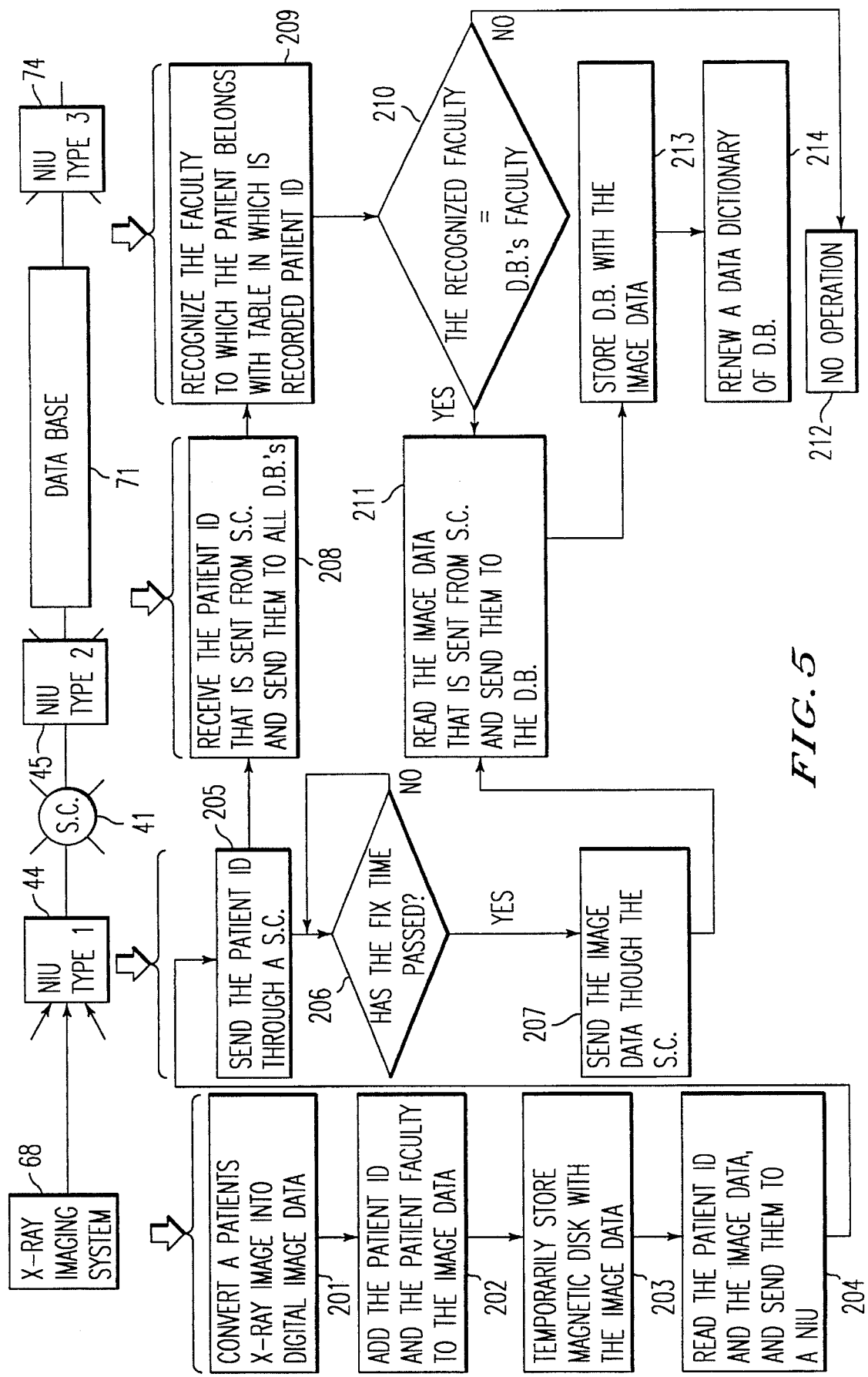
FIG. 5 is a block diagram of a fourth embodiment of an imaging system according to the present invention and includes a flow chart showing operation of the fourth embodiment.
Figure 6:
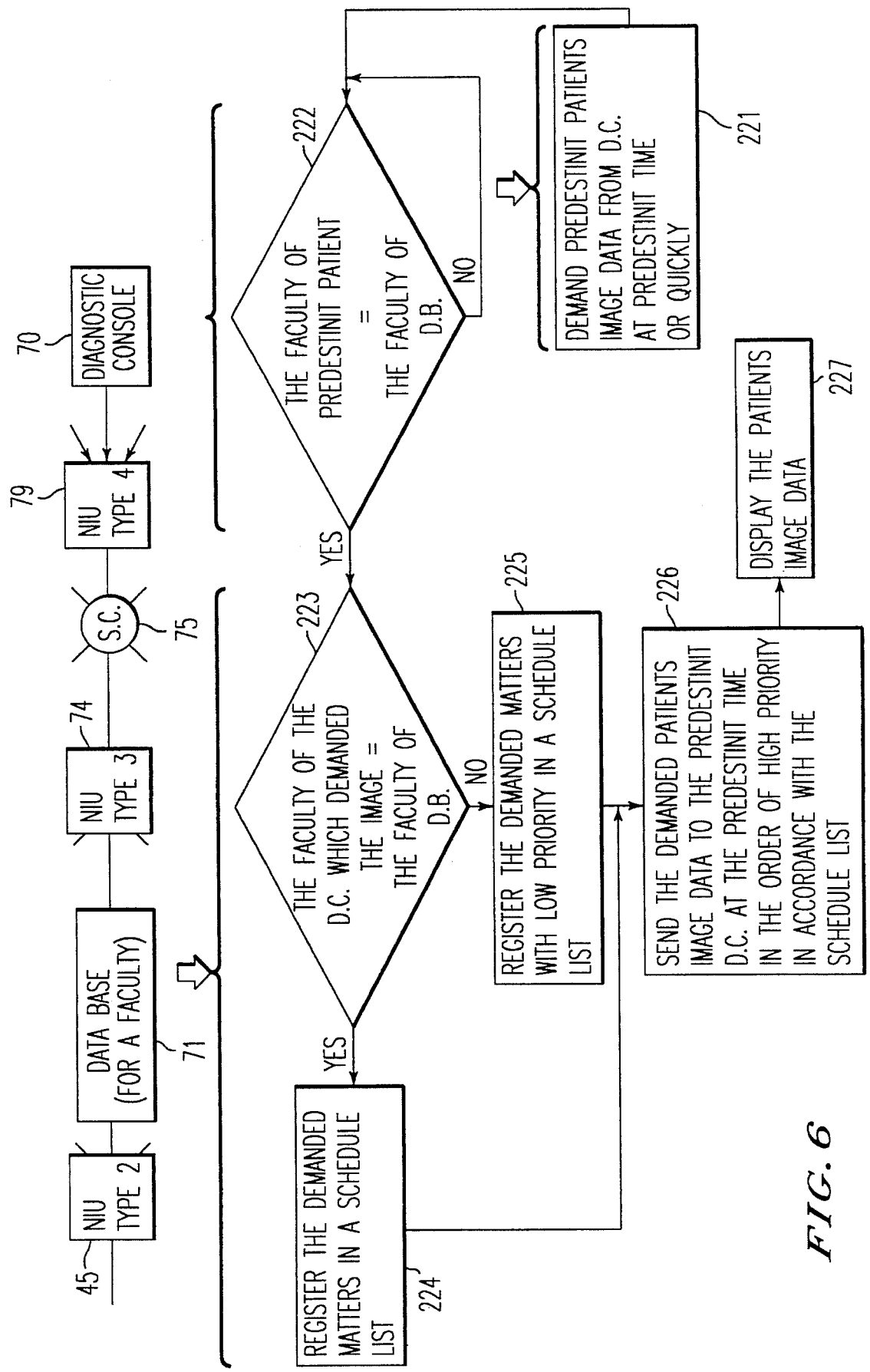
FIG. 6 is a block diagram and a flow chart of the fourth embodiment of an imaging system in a hospital according to the present invention.

Next, an explanation of another embodiment is provided by the flow chart and the block diagram shown in FIG. 5 and in FIG. 6.

FIG. 5 illustrates the signal flow and operation performed by each block 68, 44, 41, 45 and 71 when signals from patients are collected by the X-ray imaging system and stored in the data base (D.B.) 71 with the image data.

FIG. 6 illustrates the signal flow and operation performed by each block 71, 74, 75, 79 and 70 from the time a demand is made for displaying the patient's image until the image is displayed.

FIGS. 5 and 6 are drawn in accordance with actual practice in a hospital, and each includes a flow chart below the system blocks.

In FIG. 5, the operations 201, 202, 203 and 204 are performed by X-ray imaging system 68.

The operations 205, 206 and 207 are performed by NIU type I 44.

The operations 208 and 211 are performed by NIU type II 45.

The operations 209, 210, 212, 213, 214, 223, 224, and 226 are performed by Data Base 71.

The operation 222 performed by NIU type3 74.

The operations 221 and 227 performed by Diagnostic Console (D.C.) 70.

Step 201

First, signals from patients collected by X-ray imaging system 68 are converted into a digital image data.

Step 202

The digital image data have added thereto the patient ID and the patient facility automatically by a patient ID card or information from outside the computer network.

Step 203

Then, the digital image data are temporarily stored on the magnetic disc and used for diagnosis of the patient or appraisal of the image data then and there.

Step 204

After reading the patient ID and the image data from the magnetic disc, they then are sent to a NIU 44.

Step 205

The patient ID from X-ray imaging system 68 is sent through the S.C. 41.

Step 206

Then the systems waits until the image data line of the S.C. 41 is open and the facility of the patient is recognized in D.B. 71.

Step 207

After waiting, when the image data line of the S.C. 41 is open, the image data is sent through the S.C. 41 to NIU 45.

Step 208

This part of the flow chart in the NIU 45 is played as an interface between the S.C. 41 and the D.B. 71.

Step 209

The facility which the patient belongs to is recognized by means of the table in which is recorded the patient ID.

Step 210

It is determined if the recognized facility by Step 209 is equal to the faculty of D.B. 71 or not. If "yes", Step 211 is done by NIU 45. If "no", operation ceases, in Step 212.

Step 211

The image data that is sent from S.C. 41 are read and sent to the D.B. 71.

Step 213

D.B. 71 stores the image data of the same facility sent in Step 211.

Step 214

The data dictionary of D.B. 71 stores the patient's name, the patient's ID, the data and modality number that identifies the image data collected, and each patient's personal history.

When the image data is stored in D.B. by Step 213, the data dictionary of D.B. 71 is renewed.

Step 221

Then, when a user wants to refer to D.B. 71 for selected patient's image data, the user sends a command that includes the patient ID or name, selected time, the facility of D.C. 70 and image data number, from D.C. 70 through the S.C. 75 to the D.B. 71.

Step 222

At the word of command from D.C. 70, the facility of a selected patient is recognized and distinguished from the facility of D.B. 71. If both are the same, the selected patient's image data can be referred to D.B. 71 in the facility.

Step 223

The facility of the D.C. 70 which demanded the image data is compared with the facility of D.B. 71.

Step 224

When both facilities are the same, the patient ID or name, selected time, the facility of the D.C. 70 and image data number are registered in a schedule list.

Step 225

When the facility of the D.C. 70 is different from that of the D.C. 70, they are registered with lower priority then priority in step 224 in the schedule list.

Step 226

At the selected time, the requested patient's image data are read from memory in which the image data were stored by Step 213, and are sent through the NIU 74, S.C. 75, and NIU 79 to the selected D.C. 70 in the order of highest priority in accordance with the schedule list.

Step 227

The patient image data are displayed by D.C. 70. The user can get the selected patient's image data at the selected time.

According to the present invention described above, it becomes easy to make the picture diagnosis by utilizing comprehensively medical pictures of various modalities on the same patient, and the systematic management of pictures for a patient is easily done. Further the overall retrieval time can be made short, since the in-facility communication shortens the retrieval time of medical pictures in comparison with the inter-facility communication.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the U.S. is:

1. An imaging system for managing image data generated at plural functionally diverse units under the direction of attending physicians associated with respective dispersed facilities in a hospital, comprising:

an image diagnostic system including said plural functionally diverse units, each for providing medical image data based on a signal derived from a patient;

a first filing system comprising a first picture filing unit for storage of the medical image data and a first retrieval unit for retrieving data from the first picture filing unit;

a second filing system comprising a second picture filing unit for storage of the medical image data and a second retrieval unit for retrieving data from the second picture filing unit;

first network means comprising an optical fiber for transmitting said medical image data of said patient from the plural functionally diverse units of said image diagnostic system to the first and second filing systems, and from first picture filing unit to the first retrieval means and from the second picture filing unit to the second retrieval unit, at a first data transfer rate;

second network means comprising a coaxial cable for interconnecting said first filing system and the second filing system, and for transmitting medical image data between the first filing system and the second filing system at a second data transfer rate, the first data transfer rate being greater than the second data transfer rate;

recognizing means for recognizing a facility to which image data derived from a diagnosed patient is associated;

transmission control means for transmitting via the first network said image data derived from said diagnosed patient from the functionally diverse units of the image data generating section where said image data was generated to the first and second filing systems recognized by said recognizing means as being associated with the image data of the diagnosed patient.

2. The imaging system according to claim 1, wherein the image diagnostic system further includes a data compression unit for compressing the medical image data.

* * * * *